United States Patent [19]

Matsui et al.

[11] Patent Number: 4,600,689
[45] Date of Patent: Jul. 15, 1986

[54] NOVEL BILIRUBIN OXIDASE, ITS PRODUCTION AND USE

[75] Inventors: Susumu Matsui, Ootsu; Yoshio Yoshihama; Tsutomu Taniguchi, both of Kyoto, all of Japan

[73] Assignee: Takara Shuzo Co., Ltd., Kyoto, Japan

[21] Appl. No.: 649,054

[22] Filed: Sep. 10, 1984

[30] Foreign Application Priority Data

Nov. 21, 1983 [JP] Japan .............................. 58-218895
May 24, 1984 [JP] Japan .............................. 59-105604

[51] Int. Cl.$^4$ .................. C12Q 1/26; C12N 9/02; C12R 1/645
[52] U.S. Cl. ...................... 435/25; 435/189; 435/911
[58] Field of Search ..................... 435/25, 189

[56] References Cited

U.S. PATENT DOCUMENTS 4,221,844  7/1980  Wu ............................ 435/25
4,554,249  11/1985  Kosaka et al. ................. 435/10

FOREIGN PATENT DOCUMENTS 114381  8/1984  European Pat. Off. .......... 435/25
57-159487  10/1982  Japan ........................... 435/189

Primary Examiner—Lionel M. Shapiro
Attorney, Agent, or Firm—Wenderoth, Lind & Ponack

[57] ABSTRACT

The present invention relates to a novel bilirubin oxidase produced by a strain belonging to the genus Trachyderma of the class Basidiomycetes and its production, a reagent composition for bilirubin containing said novel bilirubin oxidase, a method for the quantitative determination of bilirubin in test solutions such as biological fluids with said reagent composition, and a method for applying said reagent composition to analytical methods in which the interfering effect of bilirubin needs to be eliminated.

11 Claims, 8 Drawing Figures

NOVEL BILIRUBIN OXIDASE, ITS PRODUCTION AND USE

Bilirubin is a yellow substance which is formed in the blood by degradation of hemoglobin. The rapid and accurate detection of bilirubin in blood serum is vitally important to medical diagnosis of disease states, e.g. jaundice, in human beings. Bilirubin in blood serum increases abnormally in jaundice patients, so that the degree of jaundice can be diagnosed by the measurement of bilirubin in blood serum.

For the quantitative determination of bilirubin, a chemical measurement method, called a diazo method using diazonium salts such as diazosulfanilic acid, is so far principally used (I. Kanai and M. Kanai: Manual of Clinical Assay, 28th Edition, page XII-24, published by Kinbara in 1978). This chemical measurement method, however, has defects such as specificity of reaction, complexity of operation, stimulative and corrosive properties of reagent, etc. It is therefore pointed out that this method has many problems in its introduction into automatic analytical equipment, maintenance and control of the equipment, accurate measurement and the like.

In recent years, however, a method for the quantitative determination of bilirubin with an enzyme was being developed. An enzyme which will react with bilirubin was first reported by R. Brodersen and P. Bortels [European Journal of Biochemistry, Vol. 10, 468 (1969)]. They report that an insoluble bilirubin oxidase isolated from the brain of guinea pig oxidizes bilirubin into biliverdin, but do not examine whether or not hydrogen peroxide is contained in the reaction product. Also, it is disclosed an enzyme preparation from *Agaricus bisporus* reacts specifically with bilirubin to cause a change in color (Japanese Patent Publication No. 11194/1983). The reaction product produced from said enzyme preparation and bilirubin is a substance which exhibits an absorption peak at about 510 nm and, upon excitation with 450 nm wavelength radiation, fluoresces at about 525 nm, and whether or not hydrogen peroxide is formed in this reaction depends upon how to prepare said enzyme preparation. A method for the quantitative determination of bilirubin in biological fluids with this bilirubin-specific fungal enzyme preparation is proposed, but it is very vague as to whether the reaction of said enzyme preparation with bilirubin is catalyzed by a single enzyme or a system of plural enzymes. Further, since there is no sufficient description on the property of said enzyme preparation toward bilirubin, this method may not be said to be an advantageous one for the quantitative determination of bilirubin. Also, no reference is made at all to the action of said enzyme on albumin-bound bilirubin and glucuronic acid-conjugated bilirubin either of which is one of the forms of bilirubin present in blood serum. In recent years, in the quantitative determination of bilirubin in biological fluids with bilirubin oxidase produced by the genus Myrothecium [Japanese Patent Application Kokai (Laid-open) No. 141783/1983], since said enzyme alone does not act on albumin-bound bilirubin, a method for the quantitative determination of bilirubin by the addition of a surface active agent, etc. as a reaction promoting agent is proposed [Japanese Patent Application Kokai (Laid-open) No. 17999/1984].

As described above, bilirubin oxidase is utilized in the quantitative determination of bilirubin in blood serum, but in addition to this, this enzyme is also useful to remove bilirubin which causes an error in measured values in the analysis of test samples other than bilirubin. In the measurement of glucose or cholesterol in blood serum, a colorimetric method in which glucose oxidase or cholesterol oxidase is made to act on blood serum and the formed hydrogen peroxide is trapped with peroxidase, is most popularly employed as a routine inspection method. Particularly, a color-development method with 4-aminoantipyrine-phenol has come to be a leading part of the enzymatic method, in terms of its simplicity and rapidity as well as stability of the reagent. This colorimetric method includes the measurement of the formed red quinone dye at 500 nm, but the presence of bilirubin in blood serum causes a negative error. Consequently, by causing bilirubin oxidase to act on blood serum in advance to remove bilirubin, and then causing glucose oxidase or cholesterol oxidase to act on the blood serum, the correct glucose value or cholesterol value of blood serum can be obtained In the analysis of various components in biological fluids such as blood serum, urine, etc., the following methods including the removal of bilirubin from biological fluids have so far been employed: Enzymatic quantitative determination of glucose in biological fluids by adding a trace amount of potassium ferrocyanide or potassium ferricyanide to a test sample and eliminating the interference of reducing substances such as bilirubin by utilizing oxidation-reduction potential (Japanese Patent Publication No. 25840/1980); measurement of components in biological fluids by lowering the reducing power of bilirubin with an oxidizing agent [Japanese Patent Application Kokai (Laid-open) No. 107161/1981]; measurement of intended components in biological fluids by degrading bilirubin with the foregoing bilirubin-specific fungal enzyme preparation to eliminate its interference (Japanese Patent Publication No. 11194/1983), and the like. Among the bilirubin-specific fungal enzyme preparations used in the last method above, there is one which forms hydrogen peroxide. Such preparation is not advantageous to a measurement method utilizing reaction for the quantitative determination of some components in biological fluids with oxidase, peroxidase and a hydrogen-donative chromogen. Also, in recent years, there is known a method to measure components other than bilirubin in biological fluids by eliminating the interference of bilirubin coexisting in the biological fluid using bilirubin oxidase which oxidizes bilirubin but does not form hydrogen peroxide [Japanese Patent Application Kokai (Laid-open) No. 18000/1984]. The characteristic of this method consists in that a substance which promotes the reaction of bilirubin oxidase (e.g. surface active agents) and a substance which interferes with color-development reaction (e.g. sodium fluoride) are added together with the bilirubin oxidase. But, this bilirubin oxidase, in the color-development method with peroxidase and a hydrogen-donative chromogen used for the detection of hydrogen peroxide, acts to cause quantitative oxidation-condensation of the chromogen, for example 4-aminoantipyrine and phenol, whereby the chromogen is colored red. When the substance which interferes with color-development reaction is added to the reaction solution, the action of bilirubin oxidase is disturbed at the same time so that thorough removal of bilirubin is not attained, which makes it difficult to obtain the accurate measured value of components in biological fluids.

Previously, the present inventors made a screening test on bilirubin oxidase produced by strains belonging to the class *Basidiomycetes*, and as a result, found that *Schizophyllum commune* produces bilirubin oxidase in the filtrate of cultured broth (Japanese Patent Application No. 10149/1983). Since, however, this enzyme was somewhat unstable and unsuitable for industrial production, the present inventors made a further extensive study on bilirubin oxidase produced by strains belonging to the class *Basidiomycetes*. As a result, the present inventors found that *Trachyderma tsunodae* belonging to the genus *Trachyderma* will produce a large amount of bilirubin oxidase having excellent properties in the filtrate of cultured broth, and elucidated the enzymological properties of this enzyme. Thus, the present inventors came to the conclusion that the enzyme of the present invention is a novel bilirubin oxidase different from those which are already reported. The enzyme of the present invention is designated as novel bilirubin oxidase M-1.

Referring to the outline of the present invention, the present invention relates to the novel bilirubin oxidase M-1, and also to a reagent composition for bilirubin, said composition being characterized by containing the novel bilirubin oxidase M-1.

An object of the present invention is to provide a method for the quantitative determination of bilirubin which comprises causing the foregoing reagent composition containing the novel bilirubin oxidase M-1 to act on a bilirubin-containing test solution and colorimetrically measuring the change of bilirubin produced thereby or which comprises causing 3-methyl-2-benzothiazolinone-hydrazone (hereinafter referred to as MBTH) and said reagent composition containing the novel bilirubin oxidase M-1 to act on a bilirubin-containing test solution and colorimetrically measuring the formed blue dye in an acidic condition.

Another object of the present invention is to provide a novel analytical method. In a method for analyzing components other than bilirubin in a bilirubin-containing test solution by utilizing reaction with oxidase, peroxidase and a hydrogen-donative chromogen in which method bilirubin acts as an interfering agent, said novel analytical method is characterized in that it includes (a) a step of causing the foregoing reagent composition containing the novel bilirubin oxidase M-1 to act on the test solution to eliminate the interfering effect of coexisting bilirubin and (b) a step of analyzing the desired component present in the remaining test solution.

A further object of the present invention is to provide a method for producing the novel bilirubin oxidase M-1 which comprises incubating the bilirubin oxidase M-1 producing strain belonging to the genus *Trachyderma* and separating the novel bilirubin oxidase M-1 from the cultured broth.

The present invention will be explained in more detail as follows by referring partly to the accompanying drawings wherein: FIG. 1 shows the relationship between pH and the activity of the novel bilirubin oxidase M-1 obtained by the present invention;

Figure 1:
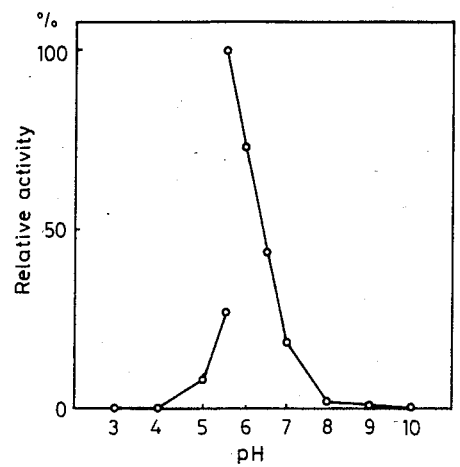

The strain used in the present invention is one belonging to the genus *Trachyderma* of the class *Basidiomycetes*, for example *Trachyderma tsunodae* K-2593. This strain was isolated from the fruit body growing on the dead trunk of beech at Mt. Daisen in Tottori Prefecture, Japan, in August, 1977.

The formal characteristics of the fruit body and spore of this strain are as follows:

An annual, stipe free.

Cap: looks half-round, spatula- or fan-form and its upper surface is flat or takes a low mountain form; 5–15 cm × 3–15 cm across; cuticle is non-shining and dark cinnamon, covered with small wrinkles and grainlike hard mucrones, assuming a coarse appearance, and generally covered with dark brown spores; flesh is almost white, and leathery and tough while growing and forms a very hard woody tissue on dry weather; and undersurface is almost white and later turns dark brown.

Pores: about 1.5 cm long, pale cinnamon; ostioles are fine.

Spores: Ganoderma type, pale yellow, takes a large ovoid-ellipsoid of $20-24\mu \times 14-16.5\mu$ in size; outer membrane is clearly distinguishable from inner membrane.

On comparing the above characteristics with the description of the following books: Rokuya Imazeki and Tsugio Hongo: Colored Illustrations of Fungi of Japan, Vols. 1 and 2 (published by Hoiku-sha Co., Osaka, Japan) and Seiya Ito: Mycological Flora of Japan, Vol. 2, No. 4, 1955 (published by Yoken-do, Tokyo, Japan), it is apparent that this strain is *Trachyderma tsunodae*. This strain is deposited at Fermentation Research Institute, Agency of Industrial Science and Technology, Japan under FERM BP-387.

Referring now to the present invention in more detail, any well-known nutrient source may be added to the culture medium, if it can be utilized by the strain used. As the carbon source, for example glycerol, glucose, starch, sucrose, maltose, lactose, dextrin, oils and fats and the like may be used. As the nitrogen source, yeast extract, peptone, corn steep liquor, defatted soybean, soybean powder, meat extract and the like are suitable. Also, inorganic substances and metallic salts such as phosphates, potassium salts, magnesium salts and the like may also be added. Since the novel bilirubin oxidase M-1 of the present invention is a copper enzyme, addition of copper sulfate to the culture medium largely increases the output of enzyme. For example, addition of 5 ppm of copper sulfate produces the novel bilirubin oxidase M-1 of 5 to 10 times by weight as compared with no addition of copper sulfate.

In the cultivation of the strain belonging to the class *Basidiomycetes*, the output of the novel bilirubin oxidase M-1 of the present invention varies largely depending upon the culture condition. Generally, however, the culture temperature is preferably 20° to 35° C., the pH of the culture medium is preferably 4 to 7, and the production of the novel bilirubin oxidase M-1 of the present invention reaches maximum by aeration/stirring culture for 3 to 15 days. In this case, it is natural that the culture condition should be determined so as to obtain a maximum output of the novel bilirubin oxidase M-1 according to strains and compositions of culture medium employed.

The novel bilirubin oxidase M-1 produced by the strain of the present invention is present in the cultured broth, and it may be separated as precipitate by adding 50 to 80 v/v% of an organic solvent (e.g. alcohol, acetone) or 20 to 60 w/v% of a precipitating agent (e.g. ammonium sulfate) to the filtrate of the cultured broth. The precipitate obtained is desalted by dialysis or Sephadex treatment to obtain a crude enzyme solution. For purifying the crude enzyme solution obtained, the solution is treated as follows: The solution is adsorbed onto a column of DEAE-Sephadex A-50 previously buffered with 0.03M phosphate buffer (pH, 7.0), and the adsorbed matter is washed with 0.1M phosphate buffer (pH, 7.0) and eluted with 0.3M phosphate buffer (pH, 7.0) to collect an active fraction. This active fraction is then concentrated and desalted by ultrafiltration, adsorbed onto a column of DEAE-Sepharose CL-6B buffered with 0.03M phosphate buffer (pH, 7.0), and the adsorbed matter is washed with 0.1M phosphate buffer (pH, 7.0) and eluted with 0.2M phosphate buffer (pH, 7.0) to collect an active fraction. This active fraction is then concentrated with a collodion membrane, gel-filtered through a column of Sephacryl S-200 previously buffered with 0.1M phosphate buffer (pH, 7.0), and the active fraction obtained is dialyzed against 0.01M phosphate buffer (pH, 7.0) and lyophilized to obtain a purified enzyme powder. This enzyme powder is a simple substance on analyzing by polyacrylamide gel disc electrophoresis.

The various properties of the novel bilirubin oxidase M-1 of the present invention are as follows:

I. Enzymological and physicochemical properties (1) Action:

The present enzyme has an action to oxidize bilirubin (albumin-bound, glucuronic acid-conjugated and free types) in the presence of oxygen far into an almost colorless substance through biliverdin and then a pale violet substance, but forms no hydrogen peroxide.

(2) Substrate specificity:

The present enzyme acts on bilirubin as well as on biliverdin, the oxidation rate of the latter, however, being about 12% of that of the former. It acts also on hydroquinone, pyrocatechol, p-phenylenediamine, pyrogallol, 4-aminoantipyrine and a monophenol, but does not act on hemin, vitamin $B_{12}$ and hemoglobin at all.

Figure 3:
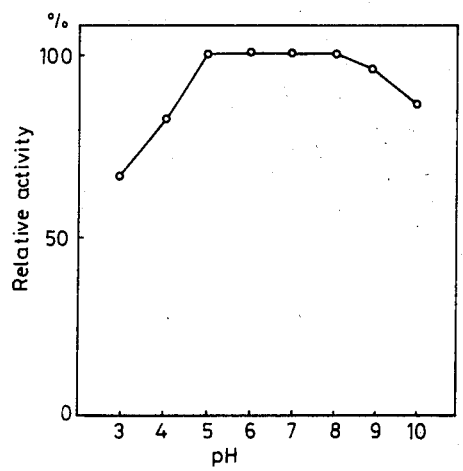
FIG. 3 shows relationship between pH and activity after 60 minutes treatment of the novel bilirubin oxidase M-1 at 37° C. and varying pHs.

(3) Optimum pH and pH stability:

The present enzyme has an optimum pH in the vicinity of 5.5 (FIG. 1), and it is stable between pH 5 and pH 9 when treated for 60 minutes at 37° C. and varying pHs (FIG. 3).

Figure 2:
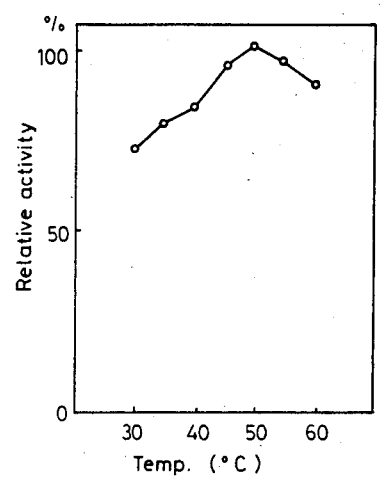
FIG. 2 shows relationship between temperature and activity.
Figure 4:
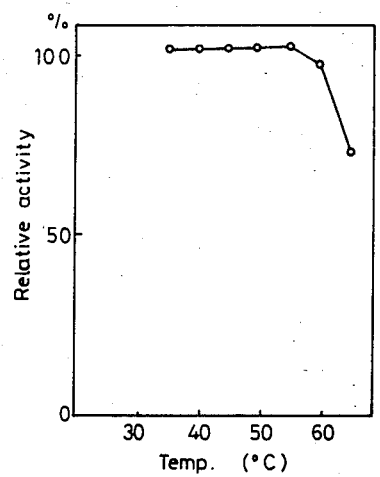
FIG. 4 shows relationship between temperature and activity after 10 minutes treatment of the novel bilirubin oxidase M-1 at a pH of 7.0 and varying temperatures.

(4) Optimum temperature and thermal stability:

The present enzyme has an optimum temperature in the vicinity of 50° C. (FIG. 2), and it is stable up to 55° C. when treated for 10 minutes at a pH of 7.0 and varying temperatures (FIG. 4).

(5) Molecular weight:

The molecular weight of the present enzyme is about 83,000 by the gel filtration method with Sephacryl S-200 (produced by Pharmacia).

(6) Homogeneity:

Disc electrophoresis was carried out using 7.5% polyacrylamide gel (pH, 9.4) to conduct protein staining and activity staining. One colored band of protein was noticed, which means that the present enzyme is a simple substance. Since this enzyme has an action to cause 4-aminoantipyrine and phenol to quantitatively develop a red color, on carrying out activity staining, a red band was noticed at the same postion as that of the colored band of protein.

(7) Isoelectric point:

The isoelectric point of the present enzyme is 3.92±0.05 by the isoelectric focusing method with Pharmalyte (pH, 3–10; produced by Pharmacia).

(8) Effect of metal ions, interfering agents, etc.:

The present enzyme is inhibited by L-ascorbic acid, sodium azide, dithiothreitol, potassium cyanide, L-cysteine, EDTA, $Fe^{2+}$ and the like (Table 1).

TABLE 1

| Additive | Percent interference (%) |
| --- | --- |
| L-ascorbic acid (1 mM) | 100 |
| Sodium azide (1 mM) | 60 |
| Sodium azide (5 mM) | 100 |
| Dithiothreitol (1 mM) | 86 |
| Potassium cyanide (1 mM) | 84 |
| L-cysteine (1 mM) | 74 |
| EDTA (1 mM) | 59 |
| $Fe^{2+}$ (1 mM) | 57 |
| Reduced glutathione (1 mM) | 38 |
| o-Phenanthroline (1 mM) | 34 |
| 2-Mercaptoethanol (1 mM) | 31 |
| α,α'-Dipyridyl (1 mM) | 30 |
| Iodoacetic acid (1 mM) | 10 |

(9) Visible absorption spectrum:

On measuring the visible absorption spectrum of a solution of the present enzyme, an absorption maximum was noticed at 610 nm, showing the presence of blue protein.

(10) Sugar content:

Disc electrophoresis was carried out using 7.5% polyacrylamide gel (pH, 9.4) to conduct PAS staining [Analytical Biochemistry, Vol. 30, 148 (1969)], and it was found that the same position as that of the colored protein was colored. This means that the present enzyme is glucoprotein containing sugar. The sugar content is about 4.5% by the phenol/sulfuric acid method.

(11) Copper content:

The copper content of the present enzyme was determined using an atomic absorption analyzer, and it was found that one mole of the present enzyme contained four moles of copper.

(12) Determination of enzymatic activity:

The enzymatic activity was obtained by measuring a decrease in the absorption at 460 nm of bilirubin. That is, reaction was carried out at 37° C. for 10 minutes using 3.0 ml of a reaction mixture containing 0.1 ml of OMEGA-chemistry Control Serum Elevated Bilirubin (produced by Hyland Co., U.S.A.), 300 micromoles of phosphate buffer (pH, 7.0) and 0.1 ml of a properly diluted enzyme solution, and a decrease in absorption at 460 nm due to bilirubin was measured. One unit of the novel bilirubin oxidase M-1 was defined as the amount of enzyme which oxidizes 1 micromole of bilirubin per minute in the foregoing reaction system.

Comparison of the novel bilirubin oxidase M-1 used in the present invention with the conventional bilirubin oxidase is shown in Table 2.

TABLE 2

|  | Novel bilirubin oxidase M-1 used in the present invention | Enzyme of *Agaricus bisporus* origin*1 | Enzyme of *Myrothecium verrucaria* origin*2 |
|---|---|---|---|
| Action | Bilirubin → biliverdin → pale green substance → pale red substance → almost colorless substance. Forms no hydrogen peroxide. | Acts on bilirubin alone to cause a change in color. Forms hydrogen peroxide. | Bilirubin → green substance → pale green substance → pale violet substance. Forms no hydrogen peroxide. |
| Substrate specificity | Bilirubin 100% Biliverdin 12% | Acts on bilirubin alone. | Bilirubin 100% Biliverdin 1% |
| Stability | Stable up to 55° C. for 10 minutes treatment at pH 7.0. Stable in the pH range of 5 to 9 for 60 minutes treatment at 37° C. | Stable in the pH range of 7.3 to 9.0. | Stable up to 40° C. for 15 minutes treatment at pH 8.0. Stable in the pH range of 6 to 10 for 60 minutes treatment at 37° C. |
| Optimum temperature | 50° C. | About 20° to about 50° C. | 40° C. |
| Optimum pH | 5.5 | 7.3 to 8.0 | 6.0 to 7.0 |
| Molecular weight | About 83,000 |  | About 52,000 |
| Isoelectric point | 3.92 ± 0.05 |  | 4.1 |
| Interfering agent | L-ascorbic acid, sodium azide, dithiothreitol, potassium cyanide |  | $Fe^{2+}$, potassium cyanide, sodium azide, thiourea |
| Visible absorption | Absorption maximum is present at 610 nm. |  | No absorption maximum is present in the vicinity of 375 nm and 460 nm. |
| Sugar content | About 4.5% |  | About 7.8% |
| Copper content | 4 Moles per mole of enzyme. |  | 1 Mole per mole of enzyme. |
| $K_m$ value | $1.67 \times 10^{-4}$ M (bilirubin) |  |  |

*1Enzyme described in Japanese Patent Publication No. 11194/1983.
*2Enzyme described in Japanese Patent Application Kokai (Laid-open) No. 141783/1983.

The reagent composition containing the novel bilirubin oxidase M-1 of the present invention may contain the common components other than said bilirubin oxidase M-1. Particularly, addition of the alkali metal salt or alkaline earth metal salt of deoxycholic acid (e.g. sodium deoxycholate) promotes the reaction. The amount of enzyme contained in the reagent composition is at least not less than 0.0001 unit, preferably 10 to 0.001 unit, and it is properly regulated according to the measurement time and uses. Sodium deoxycholate is contained at the rate of 0.01 to 1.0%, preferably 0.05 to 0.5%. In addition, the well-known buffer solutions, stabilizers for enzyme, etc. may be added if necessary. The reagent composition is provided by the well-known methods such as dissolution, lyophilization, impregnation into carrier sheet and the like. Also, the enzyme may be used in an insoluble carrier-bound form prepared according to the well-known methods.

II. Quantitative determination of bilirubin

According to the present invention, the bilirubin content of bilirubin-containing test solutions, for example biological fluids such as blood serum, urine, etc. and their pre-treatment solutions, can be determined quantitatively by utilizing the foregoing property [(1) Action] of the novel bilirubin oxidase M-1. First, the following quantitative determination method is given: Since the novel bilirubin oxidase M-1 used herein will oxidize bilirubin in the presence of oxygen far into an almost colorless substance through biliverdin and then a pale violet substance, the quantitative determination of bilirubin in biological fluids such as blood serum, urine, etc. is possible by causing the novel bilirubin oxidase M-1 to act on the test solution, and measuring the rate of a decrease in absorbance at 460 nm. For example, the bilirubin concentration of test sample (e.g. blood serum) can be measured by adding to 10 to 100 ul of the test sample 0.1 to 2.0 units of the novel bilirubin oxidase M-1 and a buffer solution (pH, 5.5 to 7.0), carrying out reaction at 20° to 40° C., preferably 37° C. for 1 to 30 minutes, preferably 5 to 10 minutes, and obtaining a difference in absorbance at 460 nm before and after addition of the novel bilirubin oxidase M-1. Also, the reaction of the novel bilirubin oxidase M-1 used herein is promoted more markedly by sodium deoxycholate than by sodium cholate which is a reaction promoter for bilirubin oxidase so far reported (Table 3).

TABLE 3

| Additive (final concentration, 0.167%) | Relative activity (%) |
|---|---|
| No addition | 100 |
| Sodium cholate | 120 |
| Sodium deoxycholate | 1650 |

As described above, the novel bilirubin oxidase M-1 used herein will act by itself on any form of bilirubin in present in blood serum, i.e. ① albumin-bound form, ② glucuronic acid-conjugated form and ③ free form. An enzyme having such a property is thus far not known. This property is superior to that of the well-known enzymes in the quantitative determination of bilirubin as well as the elimination of the bilirubin effect described later.

Figure 5:
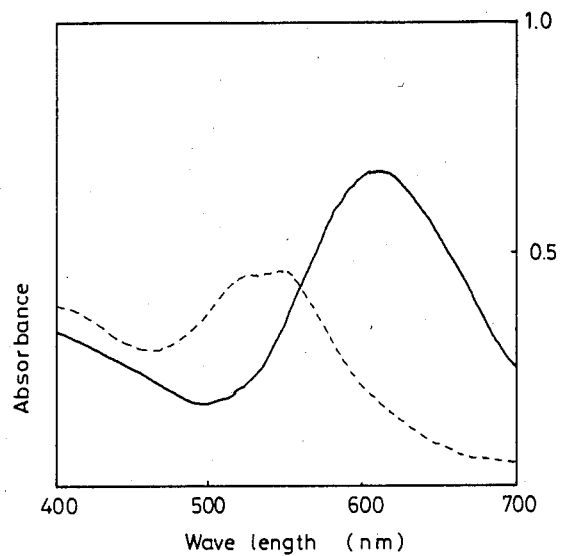
FIG. 5 shows a graph illustrating the absorption spectrum (dotted line) of a reaction product (red dye) between bilirubin and MBTH obtained with the novel bilirubin oxidase M-1 and a graph illustrating the absorption spectrum (solid line) of the blue dye produced under hydrochloric acid-acidified condition.

Secondly, the following quantitative determination method is given: The present inventors found that the novel bilirubin oxidase M-1 catalyses condensation reaction between MBTH and bilirubin, and that the quantitative determination of bilirubin is made possible by colorimetrically determining the formed condensation product in acidic condition. For example, when 0.1 to 3 micromoles of MBTH, a buffer solution (pH, 5.0 to 7.0) and 0.005 to 0.1 unit of the novel bilirubin oxidase M-1 are added to 10 to 100 ul of a test sample (e.g. blood serum), and reaction is carried out at 20° to 40° C. preferably 37° C. for 1 to 20 minutes, preferably 3 to 6 minutes, a red dye having a maximum absorption in the vicinity of 520 nm and 550 nm is formed. This red dye is converted under acidic conditions, for example under hydrochloric acid- or sulfuric acid-acidic condition, into a blue dye having a maximum absorption at 610 nm and a large molecular extinction coefficient. Consequently, bilirubin in test samples can be determined quantitatively by measuring the absorbance at 610 nm of this blue dye. For example, when 1 micromole of MBTH, 1.0 ml of 0.3 M citrate buffer (pH, 5.5) and 0.05 unit of the novel bilirubin oxidase M-1 are added to 100 ul of OMEGA-chemistry Control Serum Elevated Bilirubin (20 mg/dl; produced by Hyland Co., U.S.A.), the total volume of the mixture is made 2.0 ml, and reaction is carried out at 37° C. for 5 minutes, a red dye having a maximum absorption in the vicinity of 520 nm and 550 nm is formed. When 1.0 ml of 1N HCl is added to this substance and the system is acidified, a blue dye having a maximum absorption at 610 nm and a large molecular extinction coefficient is formed (FIG. 5). FIG. 5 is a graph illustrating the relationship between wavelength (nm) (abscissa) and absorbance (ordinate). In FIG. 5, the absorption spectrum of the red dye is shown by a dotted line and that of the blue dye is shown by a solid line.

III. Bilirubin effect-eliminating method in the analysis of components in biological fluids In analyzing various components in biological fluids such as blood serum, urine, etc. by utilizing the reaction with oxidase, peroxidase and a hydrogen-donative chromogen, a method for removing the coexisting bilirubin with the novel bilirubin oxidase M-1 will be explained. As described in the property [(6) Homogeneity] of said bilirubin oxidase M-1, this enzyme, in the color-development method with peroxidase and a hydrogen-donative chromogen intended for the detection of hydrogen peroxide, has the property of causing quantitative oxidation-binding of the chromogen, for example a 4-aminoantipyrine/phenol system, whereby the chromogen is colored red. For this reason, in a method to measure various components in biological fluids such as glucose, total cholesterol, etc., the accurate measured values of these components can be obtained by previously treating the test sample with the novel bilirubin oxidase M-1 to eliminate the effect of bilirubin which is a reducing substance, and then adding a proper interfering agent such as sodium azide [refer to the property (8) Effect of metal ions, interfering agents, etc.] to completely interfere with the action of the novel bilirubin oxidase M-1 on the hydrogen-donative chromogen.

The reaction between the novel bilirubin oxidase M-1 and a test sample can be carried out under suitable conditions according to the components to be determined present in biological fluids and determination methods employed. Generally, however, 0.01 to 0.20 unit of the novel bilirubin oxidase M-1 and a buffer solution (pH, 5.5 to 7.0) are added to 10 to 100 ul of a test sample such as blood serum, urine, etc., and after carrying out reaction at 20° to 40° C., preferably 37° C. 1 to 30 minutes, preferably 10 to 20 minutes, an interfering agent for the novel bilirubin oxidase M-1 is added so that its final concentration is 1 to 50 mM, for example sodium azide is preferably added so that its final concentration is 5 mM. The subsequent treatment may be carried out according to the common measurement method for each component. Also, in the treatment method described above, such a modification may be employed that an interfering agent for the novel bilirubin oxidase M-1 is previously added to the reagent for the measurement for each component, and then the resulting mixture is added to the test sample treated with the novel bilirubin oxidase M-1. In pre-treating the test sample with the novel bilirubin oxidase M-1, addition of sodium deoxycholate, a reaction promoting agent, (final concentration, 0.05 to 0.5%) makes it possible to reduce the amount of enzyme used in the pre-treatment and also shorten the pre-treatment time.

Next, the present invention will be illustrated with reference to the following examples, but it is not to be interpreted as being limited to the examples only.

EXAMPLE 1

Production of novel bilirubin oxidase M-1

A slant culture medium comprising 2% of glucose, 0.5% of Ebios and 1.5% of agar (Ebios medium) was inoculated with *Trachyderma tsunodae* K-2593, and cultivation was carried out by keeping the medium still at 25° C. for one week to obtain a seed fungus. Separately from this, 100 ml of a culture medium comprising 2.0% of glycerol, 0.3% of yeast extract, 1% of peptone, 0.3% of $KH_2PO_4$ and 0.1% of $MgSO_4.7H_2O$ was added to a 500-ml Erlenmeyer flask, and after sterilized at 120° C. for 20 minutes, it was cooled and inoculated with the above seed fungus. Thereafter, cultivation was carried out at 27° C. for 7 days to prepare a seed cultured broth. Separately from this, 20 liters of a culture medium comprising 2% of glycerol, 0.3% of yeast extract, 1% of peptone, 0.3% of $KH_2PO_4$, 0.1% of $MgSO_4.7H_2O$, 5 ppm of $CuSO_4.5H_2O$ and 0.03% of a defoaming agent (CB-442; produced by Nippon Yushi Co.) was added to a 30-liter jar fermenter, and sterilized at 120° C. for 20 minutes. After cooling, the culture medium was inoculated with 100 ml of the above seed cultured broth, and cultivation was carried out at 27° C. for 7 days under the condition that the aeration rate was 20 liters per minute and the stirring rate was 250 revolutions per minute. After completion of the cultivation, the mycelium was removed by filtration to obtain a culture filtrate. The novel bilirubin oxidase M-1 activity of this culture filtrate was 1.08 unit/ml. Ammonium sulfate was added to 17 liters of this culture filtrate until 60% saturation, and after allowing to stand for a whole day and night, the resulting ammonium sulfate precipitate was dialyzed for a whole day and night against a large quantity of 0.03M phosphate buffer (pH, 7.0). The crude enzyme solution thus obtained was adsorbed to a column ($\phi$11.0 cm×10 cm) of DEAE-Sephadex A-50 previously buffered with 0.03M phosphate buffer (pH, 7.0), and the adsorbed matter was washed with 0.1M phosphate buffer (pH, 7.0) and eluted with 0.3M phosphate buffer (pH, 7.0). The active fraction, an eluate, was concentrated and desalted by ultrafiltration and adsorbed to a column ($\phi$5.0 cm×5 cm) of DEAE-Sepharose CL-6B buffered with 0.03M phosphate buffer (pH, 7.0), and the adsorbed matter was washed with 0.1M phosphate buffer (pH, 7.0) and eluted with 0.2M phosphate buffer (pH, 7.0) to collect an active fraction. This active fraction was concentrated with a collodion membrane and gel-filtered through a column (φ3.6 cm ×90 cm) of Sephacryl S-200 previously buffered with 0.1M phosphate buffer (pH, 7.0). The active fraction thus obtained was dialyzed against 0.01M phosphate buffer (pH, 7.0) and after adding sucrose, a stabilizer, so that its final concentration was 0.1%, lyophilized to obtain 760 mg of a purified enzyme powder. The specific activity of this powder was 17.8 units/mg. This enzyme powder was a simple substance on analyzing by polyacrylamide gel disc electrophoresis. The purification step described above is shown in Table 4.

TABLE 4

| | Total protein content (mg) | Total activity (U) | Specific activity (U/mg) | Yield (%) |
|---|---|---|---|---|
| Culture filtrate | 211500 | 17970 | 0.085 | 100 |
| Salting-out with ammonium sulfate | 56670 | 19640 | 0.347 | 109 |
| DEAE-Sephadex A-50 | 6400 | 18510 | 2.89 | 103 |
| DEAE-Sepharose CL-6B | 831 | 15560 | 18.7 | 86.6 |
| Sephacryl S-200 | 421 | 13570 | 32.2 | 75.5 |

EXAMPLE 2

Quantitative determination of bilirubin by 460 nm-absorbance reduction method

Figure 6:
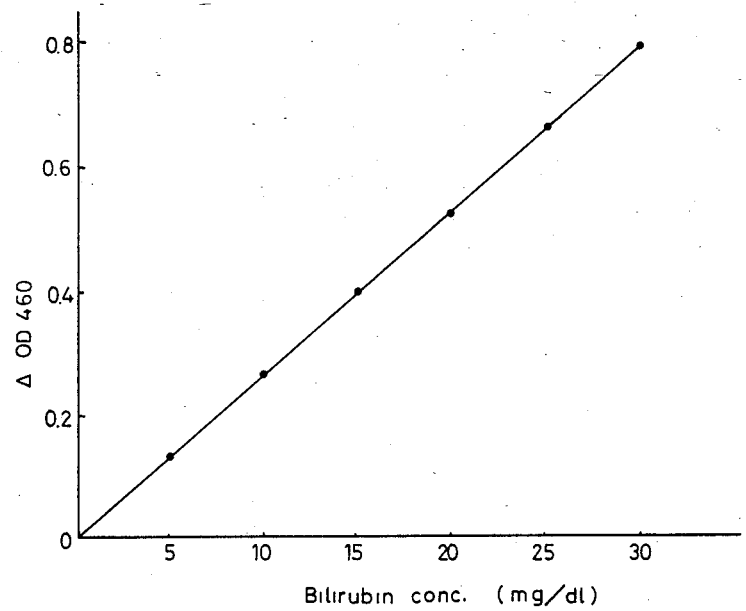
FIG. 6 shows a calibration curve obtained in Example 2, said curve representing relationship between bilirubin concentration and absorbance difference.

Bilirubin solutions containing 5 mg/dl, 10 mg/dl, 15 mg/dl, 20 mg/dl, 25 mg/dl and 30 mg/dl of bilirubin (albumin-bound type; produced by Daiichi Kagaku Yakuhin Co.) were prepared. To 0.1 ml each of these solutions were added 1.0 ml of 0.3M potassium phosphate buffer (pH, 7.0) and 0.5 unit of the novel bilirubin oxidase M-1, and after making the total volume of the solution 3.0 ml, reaction was carried out at 37° C. for 10 minutes. Thereafter, an absorbance at 460 nm ($OD_{sample}$) was measured. Separately, the same procedure as above but adding no novel bilirubin oxidase M-1 was repeated as a control test to obtain an absorbance at 460 nm ($OD_{blank}$), and a difference between $OD_{blank}$ and $OD_{sample}$, $\Delta OD_{460}$, was obtained. The results are shown in FIG. 6. FIG. 6 shows a graph illustrating a calibration curve, which represents the relationship between bilirubin concentration (mg/dl) (abscissa) and absorbance difference ($\Delta OD_{460}$) (ordinate).

As apparent from FIG. 6, by using the novel bilirubin oxidase M-1 of the present invention, it is possible to accurately determine bilirubin in biological fluids from a change in absorbance at 460 nm.

EXAMPLE 3

Quantitative determination of bilirubin by 460 nm-absorbance reduction method (effect of sodium deoxycholate)

The same bilirubin solutions as in Example 2 were prepared. To 0.1 ml each of these solutions were added 1.0 ml of 0.3M potassium phosphate buffer (pH, 7.0), 0.5 ml of 1.2% sodium deoxycholate and 0.05 unit of the novel bilirubin oxidase M-1, and after making the total volume of the solution 3.0 ml, reaction was carried out at 37° C. for 10 minutes. Thereafter, an absorbance at 460 nm ($OD_{sample}$) was measured. Separately, the same procedure as above but adding no novel bilirubin oxidase M-1 was repeated as a control test to obtain an absorbance at 460 nm ($OD_{blank}$), and a difference between $OD_{blank}$ and $OD_{sample}$, $\Delta OD_{460}$, was obtained. The results are shown in Table 7.

Figure 7:
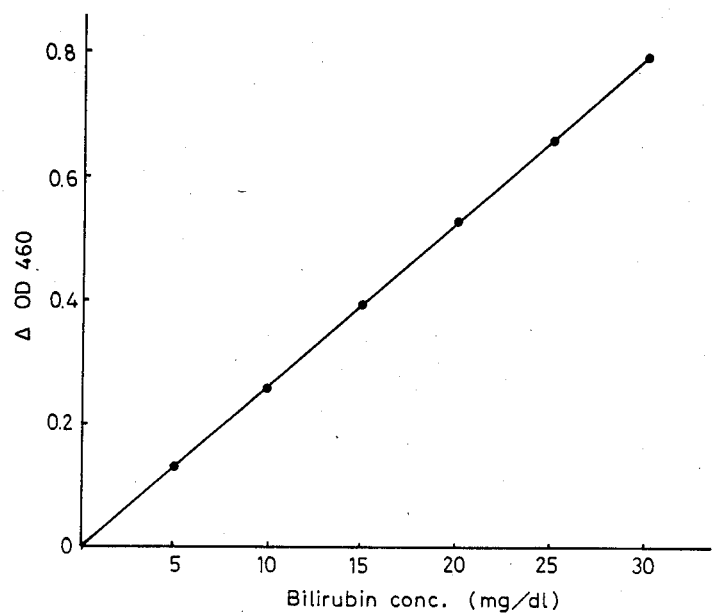
FIG. 7 shows a calibration curve obtained in Example 3, said curve representing relationship between bilirubin concentration and absorbance difference.

As apparent from FIG. 7, by adding sodium deoxycholate, which is a reaction promoting agent for the novel bilirubin oxidase M-1, to a system for the quantitative determination of bilirubin, it is possible to reduce the amount of enzyme to as large an extent as about one-tenth as compared with no addition of sodium deoxycholate.

EXAMPLE 4

Quantitative determination of bilirubin with MBTH

Figure 8:
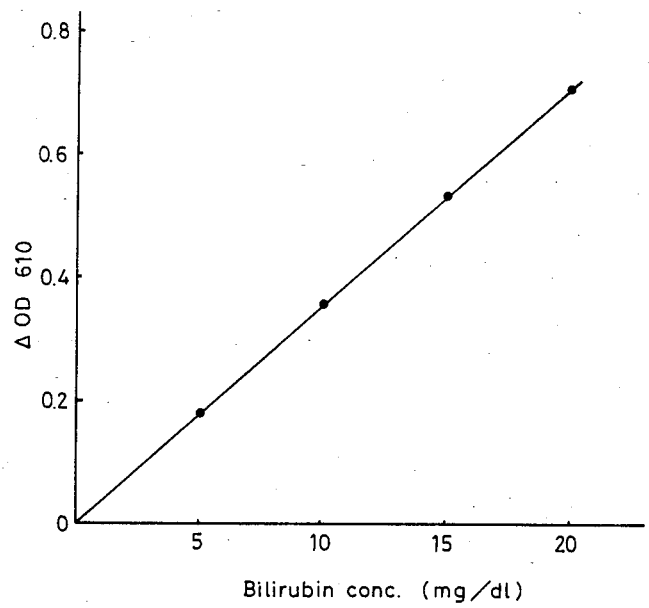
FIG. 8 shows a calibration curve obtained in Example 4, said curve representing relationship between bilirubin concentration and absorbance difference.

Bilirubin solutions containing 5 mg/dl, 10 mg/dl, 15 mg/dl and 20 mg/dl of bilirubin (albumin-bound type; produced by Daiichi Kagaku Yakuhin Co.) were prepared. To 0.1 ml each of these solutions were added 1.0 ml of 0.3M citrate buffer (pH, 5.5), 0.1 ml of 10 mM MBTH and 0.05 unit of the novel bilirubin oxidase M-1, and after making the total volume of the solution 2.0 ml, reaction was carried out at 37° C. for 5 minutes. Thereafter, 1.0 ml of 1N HCl was added and an absorbance at 610 nm ($OD_{sample}$) was measured. Separately, the same procedure as above but adding no novel bilirubin oxidase M-1 was repeated as a control test to obtain an absorbance at 610 nm ($OD_{blank}$), and a difference between $OD_{sample}$ and $OD_{blank}$, $\Delta OD_{610}$, was obtained. The results are shown in FIG. 8. FIG. 8 shows a graph illustrating a calibration curve, which represents the relationship between bilirubin concentration (mg/dl) (abscissa) and absorbance difference ($\Delta OD_{610}$) (ordinate). As apparent from FIG. 8, by using the novel bilirubin oxidase M-1 of the present invention, it is possible to accurately determine bilirubin in biological fluids from a change in absorbance at 610 nm.

EXAMPLE 5

Elimination of the interference of bilirubin in a determination system for total cholesterol in blood serum (1) Color-developing reagent:

167 mg of 4-aminoantipyrine, 1.32 g of phenol and 80 mg (100 units/mg) of peroxidase from Horseradish (type I; produced by Sigma Chemical Co., U.S.A.) were dissolved in 100 ml of 0.1M potassium phosphate buffer (pH, 7.0).

(2) Cholesterol esterase solution:

*Coriolus versicolor* K-1213 (deposited under FERM-P No. 4820) was cultivated in a medium containing cotton seed oil, peptone, corn steep liquor, etc. to obtain a culture filtrate containing cholesterol esterase activity. This culture filtrate was successively subjected to chromatography on Amberlite CG-50 column, ultrafiltration, chromatography on DEAE-Sephadex column, chromatography on SP-Sephadex column and chromatography on Sephadex G-150 column to obtain an authentic sample of purified enzyme (70 units/mg) (by the method described in Collection of Summaries of Lectures, pp. 93, at the 1982's Great Meeting of Nippon Nogei-kagaku Kai). Five milligrams of this authentic sample was dissolved in 10 ml of 0.1M potassium phosphate buffer (pH, 7.0) (35 units/ml).

(3) Cholesterol oxidase solution:

*Agrocybe pediades* K-1 (deposited under FERM-P No. 4343) was cultivated in a medium containing soluble starch, soybean oil, peptone, etc. to obtain a culture filtrate containing cholesterol oxidase activity. This culture filtrate was successively subjected to chromatography on Amberlite CG-50 column, ultrafiltration, chromatography on DEAE-Sephadex column, chromatography on SP-Sephadex column and chromatography on Sephadex G-100 column to obtain an authentic sample of purified enzyme (15 units/mg) (by the method described in Collection of Summaries of Lectures, pp. 99, at the 1978's Great Meeting of Nippon Nogeikagaku Kai). Ten milligrams of this authentic sample was dissolved in 5 ml of 0.1M potassium phosphate buffer (pH, 7.0) (30 units/ml).

(4) Procedure:

To a test tube were added 0.1 ml of the novel bilirubin oxidase M-1 (0.02 unit), 1 ml of 0.3M potassium phosphate buffer (pH, 7.0), 0.3 ml of 3% Triton X-100 solution, 0.02 ml of Control Serum (produced by Hyland Co., U.S.A.) and 0.02 ml of 20 mg/dl albumin-bound bilirubin (produced by Daiichi Kagaku Yakuhin Co.), and reaction was carried out with shaking in a constant-temperature incubator (37° C.) for 20 minutes. Thereafter, 0.3 ml of 50 mM sodium azide, 0.3 ml of the color-developing reagent, 0.1 ml of the cholesterol esterase solution, 0.1 ml of the cholesterol oxidase solution and 0.76 ml of distilled water were added, and after carrying out reaction for 5 minutes, an absorbance at 500 nm was measured. Separately, control tests including no treatment with the novel bilirubin oxidase M-1 and no addition of albumin-bound bilirubin, respectively, were carried out to measure the absorbance. By the means as described above, elimination of the color-development interference of bilirubin in a determination system for total cholesterol in blood serum was examined using the enzyme of the present invention. The results are shown in Table 5.

TABLE 5

|  | OD$_{500\ nm}$ | Percentage (%) |
|---|---|---|
| No addition of albumin-bound bilirubin | 0.160 | 100 |
| Novel bilirubin oxidase M-1 |  |  |
| No treatment | 0.127 | 79.4 |
| 20 Minutes treatment | 0.158 | 98.8 |

As apparent from Table 5, by using the method of the present invention, it became possible to eliminate the interference of bilirubin thereby to obtain the accurate value of total cholesterol in blood serum.

EXAMPLE 6

Elimination of the interference of bilirubin in a determination system for total cholesterol in blood serum (effect of sodium deoxycholate)

(1) Color-developing reagent:

The color-developing reagent of Example 5 was used.

(2) Cholesterol esterase solution and cholesterol oxidase solution:

The enzyme solutions of Example 5 were used.

(3) Procedure:

To a test tube were added 0.1 ml of the novel bilirubin oxidase M-1 (0.002 unit), 1.0 ml of 0.3M potassium phosphate buffer (pH, 7.0), 0.02 ml of Control Serum (produced by Hyland Co., U.S.A.), 0.02 ml of 20 mg/dl albumin-bound bilirubin (produced by Daiichi Kagaku Yakuhin Co.), 0.25 ml of 1.2% sodium deoxycholate and 0.11 ml of distilled water, and reaction was carried out with shaking in a constant-temperature incubator (37° C.) for 10 minutes. Thereafter, 0.3 ml of 3% Triton X-100 solution, 0.3 ml of 50 mM sodium azide, 0.3 ml of the color-developing reagent, 0.1 ml of the cholesterol esterase solution, 0.1 ml of the cholesterol oxidase solution and 0.4 ml of distilled water were added, and after carrying out the reaction for 5 minutes, an absorbance at 500 nm was measured. Separately, control tests including no treatment with the novel bilirubin oxidase M-1 and no addition of albumin-bound bilirubin, respectively, were carried out to measure the absorbance. By the means as described above, the effect of sodium deoxycholate to eliminate the color-development interference of bilirubin in a determination system for total cholesterol in blood serum was examined. The results are shown in Table 6.

TABLE 6

|  | OD$_{500\ nm}$ | Percentage (%) |
|---|---|---|
| No addition of albumin-bound bilirubin | 0.159 | 100 |
| Novel bilirubin oxidase M-1 |  |  |
| No treatment | 0.126 | 79.2 |
| 10 Minutes treatment | 0.158 | 99.4 |

As apparent from Table 6, by using sodium deoxycholate in eliminating the interference of bilirubin, it became possible to reduce the amount of enzyme used in the pre-treatment and also to shorten the pre-treatment time.

EXAMPLE 7

Elimination of the interference of bilirubin in a determination system for glucose in blood serum (1) Color-developing reagent:

The color-developing reagent of Example 5 was used.

(2) Glucose oxidase solution:

20 mg of glucose oxidase (produced by TOYOBO Co.; 100 units/mg) was dissolved in 2 ml of 0.1M potassium phosphate buffer (pH, 7.0) (1000 units/ml).

(3) Procedure:

To a test tube were added 0.1 ml of the novel bilirubin oxidase M-1 (0.02 unit), 1 ml of 0.3M potassium phosphate buffer pH, 7.0), 0.02 ml of Control serum (produced by Hyland Co., U.S.A.) and 0.02 ml of 20 mg/dl albumin-bound bilirubin (produced by Daiichi Kagaku Yakuhin Co.), and reaction was carried out with shaking in a constant-temperature incubator (37° C.) for 20 miutes. Thereafter, 0.3 ml of 50 mM sodium azide, 0.3 ml of the color-developing reagent, 0.1 ml of the glucose oxidase solution and 1.16 ml of distilled water were added, and after carrying out reaction for 10 minutes, an absorbance at 500 nm was measured. Separately, control tests including no treatment with the novel bilirubin oxidase M-1 and no addition of albumin-bound bilirubin, respectively, were carried out to measure the absorbance. By the means as described above, elimination of the color-development interference of bilirubin in a determination system for glucose in blood serum was examined using the enzyme of the present invention. The results are shown in Table 7.

TABLE 7

|  | OD$_{500\ nm}$ | Percentage (%) |
|---|---|---|
| No addition of albumin-bound bilirubin | 0.193 | 100 |
| Novel bilirubin oxidase M-1 |  |  |
| No treatment | 0.148 | 76.7 |

TABLE 7-continued

| | OD$_{500\ nm}$ | Percentage (%) |
|---|---|---|
| 20 Minutes treatment | 0.192 | 99.5 |

As apparent from Table 7, by using the method of the present invention, it became possible to eliminate the interference of bilirubin thereby to obtain the accurate value of glucose in blood serum.

What is claimed is:

1. A bilirubin oxidase M-1 having the following physicochemical properties:
    (1) Action: Has an action to oxidize bilirubin in the presence of oxygen far into an almost colorless substance through biliverdin and then a pale violet substance, but forms no hydrogen peroxide;
    (2) Substrate specificity: Acts on bilirubin and to some degree on biliverdin as well as on phenol, catechol and hydroquinone;
    (3) Optimum pH and pH stability: Has an optimum pH in the vicinity of 5.5, and is stable between pH 5 and pH 9 for 60 minutes treatment at 37° C.
    (4) Optimum temperature and thermal stability: Has an optimum temperature in the vicinity of 50° C. and is stable up 55° C. for 10 minutes treatment at a pH of 7.0;
    (5) Molecular weight: About 83,000 (gel filtration method);
    (6) Isoelectric point: 3.92±0.05;
    (7) Interfering agent: Inhibited by sodium azide, L-ascorbic acid, dithiothreitol and potassium cyanide;
    (8) Visible absorption spectrum: Has an absorption maximum in the vicinity of 610 nm;
    (9) Sugar content: Contains about 4.5% of sugar;
    (10) Copper content: Contains 4 moles of copper per mole.

2. The reagent composition for bilirubin characterized in that said composition contains the bilirubin oxidase M-1 of claim 1.

3. The reagent composition for bilirubin as described in claim 2 containing the salt of deoxycholic acid.

4. A method for the quantitative determination of bilirubin wherein a reagent composition for bilirubin containing the bilirubin oxidase M-1 of claim 1 is caused to act on a bilirubin-containing test solution and a change in bilirubin caused thereby is measured colorimetrically.

5. The method as described in claim 4, wherein said composition contains the salt of deoxycholic acid.

6. The method for the quantitative determination of bilirubin wherein 3-methyl-2-benzothiazolinone-hydrazone and a reagent composition for bilirubin containing the bilirubin oxidase M-1 of claim 1 are added to a bilirubin-containing test solution, the mixed solution is brought into reaction, and after acidifying the reaction solution, bilirubin is quantitatively determined by the colorimetric method.

7. In a method for analyzing components other than bilirubin in a bilirubin-containing test solution by utilizing reaction with oxidase, peroxidase and a hydrogen-donative chromogen in which method bilirubin acts as an interfering agent, the improvement wherein said method includes (A) a step of causing a reagent composition for bilirubin containing the bilirubin oxidase M-1 of claim 1 to act on the test solution to eliminate the interfering effect of the coexisting bilirubin and (b) a step of analyzing the desired component present in the remaining test solution.

8. The analytical method as described in claim 7, wherein an interfering substance for the bilirubin oxidase M-1 is added after the step (a) has been completed, and then the step (b) is carried out.

9. The analytical method as described in claim 7, wherein said composition contains the salt of deoxycholic acid.

10. A method for producing the bilirubin oxidase M-1 of claim 1 which comprises cultivating the bilirubin oxidase M-1 producing strain *Trachyderma tsunodae* K-2593 (FERM BP-387) to produce a culture broth containing bilirubin oxidase M-1 and recovering said bilirubin oxidase M-1 from said culture broth.

11. An analytical method as described in claim 8 wherein said composition contains the salt of deoxycholic acid.

* * * * *